United States Patent [19]

Luther

[11] 4,100,393
[45] Jul. 11, 1978

[54] METHOD FOR MAKING A CANNULA USING A LASER AND THE CANNULA MADE THEREBY

[76] Inventor: Ronald B. Luther, 1737 Bayport Way, Newport Beach, Calif. 92660

[21] Appl. No.: 766,735

[22] Filed: Feb. 8, 1977

[51] Int. Cl.² .............................................. B23K 9/00
[52] U.S. Cl. .......................................... 219/121 LM
[58] Field of Search ................... 219/121 L, 121 LM; 128/214.2, 214.4

[56] References Cited

U.S. PATENT DOCUMENTS

| 3,534,472 | 10/1970 | DeJong et al. | 219/121 LM |
| 3,651,807 | 3/1972 | Huggins | 128/214.4 |
| 3,668,028 | 6/1972 | Short | 219/121 L |
| 3,802,927 | 4/1974 | Gomada | 219/121 L |

Primary Examiner—J. V. Truhe
Assistant Examiner—Fred E. Bell
Attorney, Agent, or Firm—Shlesinger, Arkwright, Garvey & Dinsmore

[57] ABSTRACT

A process for making a removable cannula using a laser to make a longitudinal cut and a longitudinal score line in the cannula wall and the cannula made thereby.

4 Claims, 14 Drawing Figures

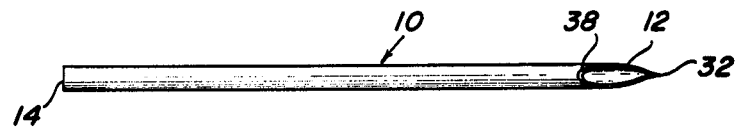
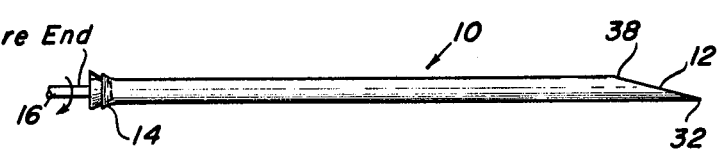
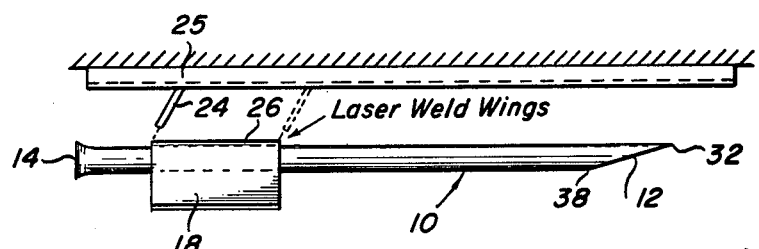
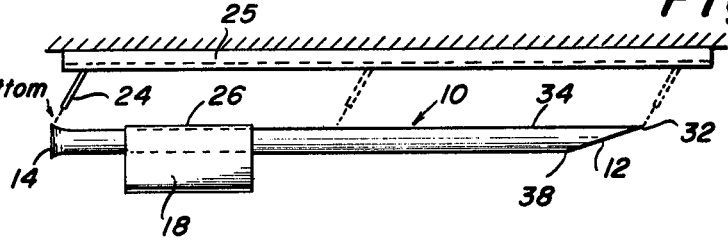
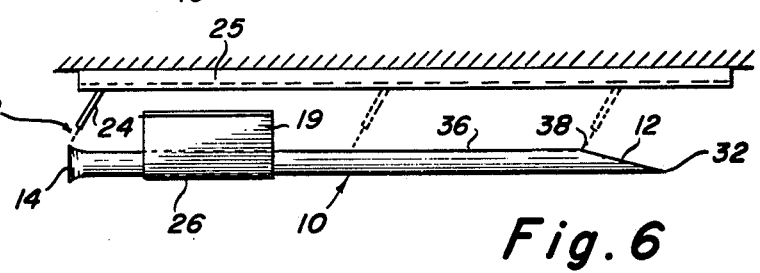

METHOD FOR MAKING A CANNULA USING A LASER AND THE CANNULA MADE THEREBY

HISTORICAL BACKGROUND

This invention relates to cannulae, more specifically to cannulae used in the introduction of intravenous, intramuscular, intraarterial or other intracorporeal catheters or tubular devices into bodies and has to do with their manufacture.

Such a cannula is located at the insertion end of the catheter where it is used to make the puncture through which the catheter is inserted into a body. A problem in the art has been presented by the need for removal of the cannula after the catheter has been inserted. The cannula being very sharp can cause damage to the catheter or to body tissue if left in place.

One approach to the problem has involved the use of a through-the-cannula catheter in which a cannula is positioned as a sleeve around the insertion end of the catheter. The cannula slides longitudinally on the catheter so that after a puncture is made, the cannula may be held in position while the catheter is slid the desired length into the body and then is removed from the body by sliding it up the catheter away from the body leaving the catheter still inserted in the body. Although this solves the problem of patient discomfort, the cannula is still positioned around the catheter and could cut or puncture the catheter which is usually made from flexible synthetic resin material.

This problem has been solved by the use of a removable cannula which generally has a longitudinal slit running the length of its body, a longitudinal weakened seam consisting of scoring or perforations opposite the longitudinal slit and wings or finger grips attached thereto as shown in U.S. Pat. Nos. 3,359,978, 3,584,625, 3,592,193, 3,596,658 and 3,598,118. These features combine to permit an operator to peel the cannula off the catheter after it is slid out of the body by bending and breaking it in halves along the longitudinal seam. Thus the cannula is removed entirely and presents no further problem.

However, to date there has been no satisfactory method for making such removable cannulae which have usually been shaped from sheet metal. There is no method available for making such removable cannulae from ordinary cannula stock.

SUMMARY OF THE INVENTION

Therefore, a purpose of this invention is to provide a better method for making a removable cannula.

A purpose is to provide a better removable cannula than hereto available.

A purpose is to provide a method for making such a cannula from conventional cannula stock rather than from sheet metal.

A further purpose is to provide a method for making a removable cannula which will minimize the dimensions of cuts, perforations and scores in the cannula so as to preserve its overall smoothness to an extent not possible before.

Another purpose is to provide a removable cannula which will have none of the force lines, sharp edges, and burrs caused by conventional machining operations involving cutting and perforating tools.

A purpose is to provide a removable cannula having minimum aberrations as compared with a conventional cannula.

A further purpose is to provide a method for making a removable cannula which will more effectively control the brittleness of the cannula at the score line about which the cannula is bent and broken into two halves when being removed from its catheter.

These objects are achieved by a process for making a cannula in which a laser is used to treat cannula stock to make a longitudinal cut and a longitudinal score circumferentially spaced from the longitudinal cut. The laser is also used to weld finger grips to the cannula and to remove the sharp edge at the distal area of the cannula's bevel. The posterior end of the cannula is flared to prevent its cutting the catheter when being moved relative to it.

DESCRIPTION OF THE DRAWINGS

FIG. 1 is a side elevational view of one type of cannula stock used to make the cannula of this invention.

FIG. 2 is a top plan view of the cannula stock of FIG. 1.

FIG. 3 is a side elevational view showing the flaring of the cannula stock.

FIG. 4 is a side elevational view showing the spot welding of finger grips to the cannula stock using a laser.

FIG. 5 is a side elevational view showing the scoring of the cannula stock using a laser.

FIG. 6 is a side elevational view showing the cutting of the cannula stock using a laser.

FIG. 7 is a perspective view of a finished removable cannula having one type of finger grip.

DETAILED DESCRIPTION

Figure 8:
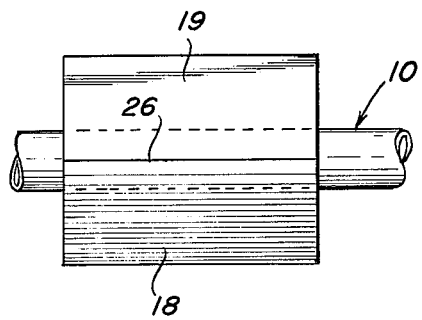
FIG. 8 is an enlarged fragmentary bottom plan view of the cannula stock showing the detail of one form of finger grip structure.

FIGS. 1 and 2 show one type of cannula stock 10 which will be processed to make the removable cannula of this invention. The cannula stock 10 shown in FIGS. 1 and 2 is a conventional cannula having a beveled anterior end 12 for making an insertion cut.

The term "cannula stock" should not be interpreted this restrictively however. It encompasses any tubular article which can be processed into the removable cannula end product. The anterior end 12 may be supplied beveled or unbeveled. If unbeveled, then beveling is supplied by standard techniques. The beveling may be a single bevel or a double bevel. The posterior end 14 may be supplied flared or unflared. If unflared as shown in FIGS. 1 and 2 then flaring should be provided as shown in FIG. 3 by a conventional flaring tool 16. This flare permits the easy safe retraction of the cannula from the insertion cut by sliding it up the catheter without abrading or lacerating the catheter.

The cannula stock 10 may be simply uncut tubing of indeterminate length which must then be cut to size.

The diameter of the cannula stock 10 may be whatever is appropriate in the catheterization art. A gauge of 10 to 25 is usual. Similarly, the length of each cannula is not critical but may be whatever length would be proper for optimum utility in catheterization.

The metal used in the cannula stock 10 may be any metal but stainless steel is preferred.

With the cannula stock's anterior and posterior ends 12, 14 beveled and flared respectively the cannula stock 10 is ready for further processing.

Figure 9:
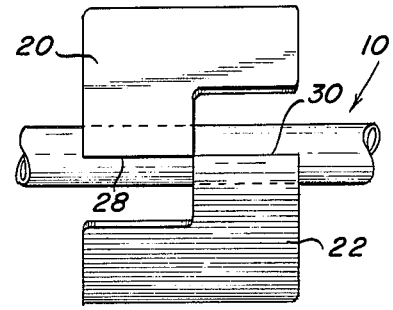
FIG. 9 is an enlarged fragmentary bottom plan view similar FIG. 8 showing the detail of a modified form of finger grip structure.
Figure 14:
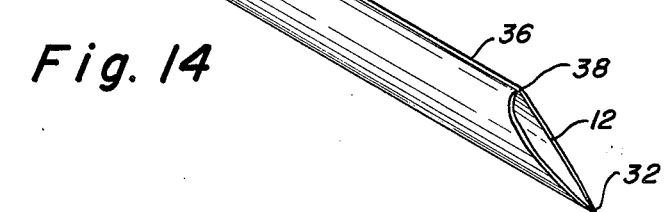
FIG. 14 is a perspective view of a finished removable cannula having a modified type of finger grip structure.

The cannula finger grips or wings 18, 19 are next attached to the cannula stock 10 as shown in FIG. 4. These facilitate handling of the finished cannula and are used to bend and break the cannula for removal from a catheter. The finger grips may be formed by a punch press or other suitable apparatus and may be of any appropriate shape such as the rectangle finger grips 18, 19 of FIGS. 4 through 8 or as the finger grips 20, 22 of FIGS. 9 and 14. Although their exact location along the length of the cannula stock 10 is not critical, it is preferred that they be situated toward the posterior end 14 to leave more room for insertion into a body puncture. The finger grips 18, 19 or 20, 22 are attached to the cannula stock 10 by spot welding which may be done by a laser apparatus 24 movably mounted on a support 25 as shown in FIG. 4 and are located so that their bases (26 in the case of 18, 19, and 28, 30 respectively in the case of 20, 22) are on a longitudinal line whose anterior end is at the bevel frontal area or tip 32. The angle at which the finger grips 18, 19 or 20, 22 are spot welded to the cannula stock 10 is not critical.

Next the laser 24 is used to make a straight longitudinal score 34 from one end of the cannula stock 10 to the other on the longitudinal line whose anterior end is at the bevel frontal area or tip 32. The longitudinal score 34 and the finger grips 18, 19 or 20, 22 are located on this specific longitudinal line so that the longitudinal cut 36, which when made will be circumfirentially spaced approximately 180° from the longitudinal score 34, will be on a longitudinal line terminating in the bevel's distal area 38 where it will interfere least with the cutting integrity of the beveled anterior end 12.

Figure 10:
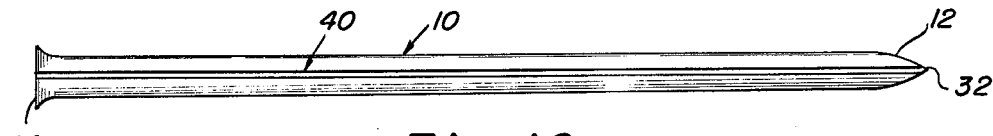
FIG. 10 is a bottom plan view of the cannula stock showing one type of score line structure.
Figure 11:
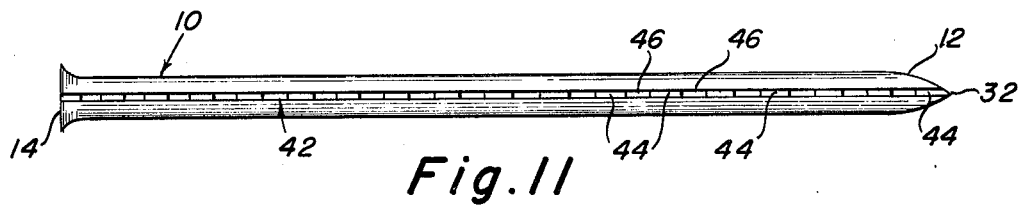
FIG. 11 is a bottom plan view of the cannula stock showing a modified type of score line structure.
Figure 12:
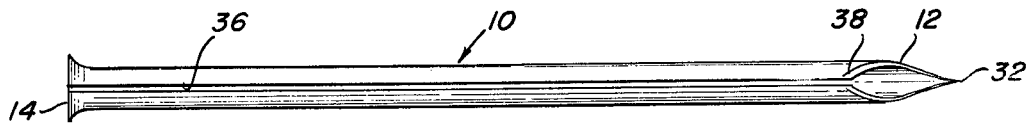
FIG. 12 is a top plan view of the cannula stock showing the longitudinal cut.
Figure 13:
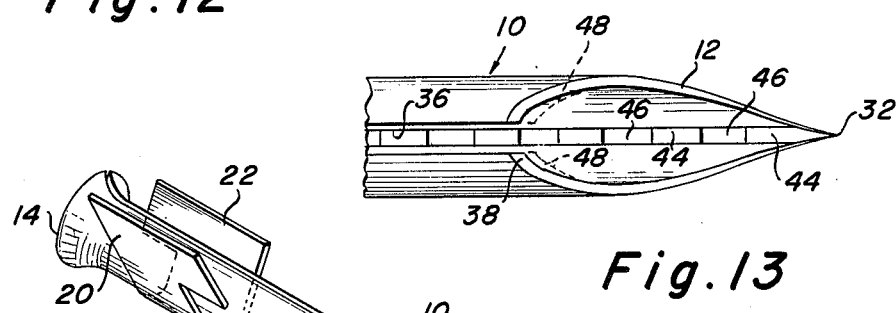
FIG. 13 is an enlarged fragmentary top plan view of the anterior end of the cannula stock.

This score 34 which may be variously characterized as a groove, partial cut or notch may be uniform in character along its entire length as shown by the score 40 of FIG. 10 or may be a score 42 as shown in FIG. 11 having a series of alternating grooves 44 and complete perforations 46 of the cannula stock wall. Broadly speaking the structure of this score 34 may be any laser made structure which will weaken the cannula wall along a longitudinal line so that when the finished cannula is to be removed from the catheter, it will easily bend and break along this score line 34. The longitudinal score 34 may be a discontinuous structure in the making of which the laser 24 is used to treat only portions of the cannula stock wall on the longitudinal line ending at the bevel frontal area or tip 32. The laser treatment also serves to enbrittle or harden the remaining metal left at the score line 34.

If the longitudinal score's anterior end will be at the bevel frontal area or tip 32 and if the score 34 is an alternating series of grooves and perforations 42, the laser 24 must be so regulated as to place a groove 44 rather than a perforation 46 at the bevel tip 32 in order to preserve the cutting integrity of the beveled anterior end 12.

The laser 24 is then used to make the straight longitudinal cut 36 through the wall of the cannula stock 10 on a longitudinal line circumfirentially spaced approximately 180° from the longtitudinal score 34. This cut 36 is situated so that its anterior end will be at the bevel's distal area 38. As previously mentioned, location of the anterior end here will interfere least with the cutting integrity of the beveled anterior end 12. 90% of the work of a successful penetration by the point of a cannula is done by the first ⅓ of the bevel. 99% of the work and any resulting discomfort is done by the first ¾ of the length of the bevel. Therefore the small opening at the anterior end of the longitudinal cut 36 will not result in any patient discomfort or trauma since located in the distal area 38 of the beveled anterior end 12.

The beveled anterior end 12 has about its distal area 38 a sharp inner edge 48 which can cut into a catheter if the finished cannula should slide forward on the catheter when in use. This sharp edge 48 is removed by the laser 24.

Laser treatment results in the evaporation of some metal and the melting of a further portion in the immediate contact area leaving after treatment smooth solidified surfaces in the treatment area rather than the rough surfaces having forced lines, sharp edges and burrs caused by conventional cutting and perforating tools.

Laser treatment may cause the formation of metal beads (not shown) as the molten metal solidifies. Subsequent to laser treatment, therefore, the cannula stock 10 is treated to remove these metal beads or laser machining burrs in a deburring apparatus.

The cannula 10 is then polished and the bevel surfaces are honed if they have not already been. Finally the completed cannula is sterilized and packaged.

The process has been described in the order of first spot welding the finger grips, next making the longitudinal score and finally making the longitudinal cut. However, this order is not critical. The steps may be performed in any order.

The process lends itself to as much mechanization as is practicable and may be performed in an automated apparatus in which the laser is moved, attenuated and switched under a computer control which integrates laser action with cannula stock manipulation. Automatic cutting, flaring and beveling tools may be part of the apparatus. After laser treatment, the cannulae are advanced to a mechanical deburring and polishing station.

All laser movement is accomplished by linear electric motors on cross feeds and rotation fixtures. The linear motors are servo-controlled by the cannula stock manipulation mechanism and programmed by computer to cannula and finger grip dimensions. The intensity of the laser is controlled by Q switching with pulses of variable duration and frequency, appropriately programmed for cannula and finger grip material characteristics and dimensions.

The mechanism may be built so that the laser head moves relative to the cannula stock or vise versa.

While this invention has been described as having a preferred design, it will be understood that it is capable of further modification. This application, is, therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What is claimed is:

1. A method for making a removable catheterization cannula from tubular cannula stock having a bevel forming a tip end and a distal area comprising the steps of:
    (a) supporting a piece of tubular cannula stock for work operations;
    (b) applying to the outside of the wall of said stock from one end of said stock to the other on a straight longitudinal line whose anterior end is at the bevel distal area a laser beam regulated in intensity and duration to cut completely through the wall of said stock to form a straight longitudinal slot in said stock ending at the bevel distal area;
    (c) applying to the inside of the wall of said stock opposite said slot from one end of said stock to the other on a straight longitudinal line whose anterior end is at the bevel tip a laser beam regulated in intensity and duration to form a weakened fracture line in the wall of said stock;
    (d) contact positioning on the outside of the wall of said stock adjacent said fracture line finger grips so that said finger grips extend on either side of said fracture line;
    (e) applying to the area of contact between said stock and said finger grips a laser beam of such intensity and duration as to weld said finger grips to said stock; and
    (f) removing the finished tubular cannula stock from the support.

2. The method of claim 1 wherein said step of forming a weakened fracture line comprises applying to said longitudinal line a laser beam regulated in intensity and duration to alternately groove and perforate the wall of said stock while embrittling the remaining metal at said longitudinal line and leaving a groove at the bevel tip.

3. The method of claim 2 and including the step of applying a laser beam to the sharp edges of the bevel distal area of such intensity and duration as to remove said sharp edges.

4. A removable catheterization cannula made by the process of claim 2.

* * * * *